United States Patent
Wood

[11] Patent Number: 6,013,824
[45] Date of Patent: Jan. 11, 2000

[54] REDISTRIBUTING SILALKYLENES IN AN ALKYL-RICH SILALKYLENE-CONTAINING RESIDUE

[75] Inventor: Larry Herbert Wood, Campbellsburg, Ky.

[73] Assignee: Dow Corning Corporation, Midland, Mich.

[21] Appl. No.: 09/205,317

[22] Filed: Dec. 1, 1998

[51] Int. Cl.[7] .................................................. C02F 7/08
[52] U.S. Cl. ............................................ 556/467; 556/468
[58] Field of Search ..................................... 556/467, 468

[56] References Cited

U.S. PATENT DOCUMENTS

| | | | |
|---|---|---|---|
| 2,380,995 | 8/1945 | Rochow | 260/607 |
| 2,488,487 | 11/1949 | Barry et al. | 260/448.2 |
| 2,598,435 | 5/1952 | Mohler et al. | 260/448.2 |
| 2,681,355 | 6/1954 | Barry et al. | 260/448.2 |
| 3,639,105 | 2/1972 | Atwell et al. | 23/366 |
| 4,079,071 | 3/1978 | Neale | 260/448.2 |
| 4,393,229 | 7/1983 | Ritzer et al. | 556/430 |
| 4,958,040 | 9/1990 | Yoshioka et al. | 556/467 |
| 5,175,329 | 12/1992 | Bokerman et al. | 556/467 |
| 5,292,909 | 3/1994 | Chadwick et al. | 556/468 |
| 5,292,912 | 3/1994 | Chadwick et al. | 556/468 |
| 5,321,147 | 6/1994 | Chadwick et al. | 556/466 |
| 5,326,896 | 7/1994 | Chadwick et al. | 556/466 |
| 5,430,168 | 7/1995 | Ferguson et al. | 556/467 |
| 5,606,090 | 2/1997 | Brinson et al. | 556/467 |
| 5,627,298 | 5/1997 | Freeburne et al. | 556/467 |
| 5,629,438 | 5/1997 | Freeburne et al. | 556/466 |

*Primary Examiner*—Paul F. Shaver
*Attorney, Agent, or Firm*—Melvin D. Fletcher; William F. Boley

[57] ABSTRACT

A process for redistributing an alkyl-rich silalkylene-containing residues. The process comprises contacting an alkyl-rich silalkylene-containing residue with a halosilane selected from the group consisting of alkyltrihalosilanes and tetrahalosilanes in the presence of an effective amount of a redistribution catalyst at a temperature within a range of about 150° C. to 500° C. thereby forming a redistribution product comprising dialkyldihalosilane. At least a portion of the catalyst in the present process may be formed in situ during conduct of the direct process and isolation of the resulting monosilanes.

20 Claims, No Drawings

REDISTRIBUTING SILALKYLENES IN AN ALKYL-RICH SILALKYLENE-CONTAINING RESIDUE

BACKGROUND OF INVENTION

The present invention is a process for redistributing an alkyl-rich silalkylene-containing residue. The process comprises contacting an alkyl-rich silalkylene-containing residue with a halosilane selected from the group consisting of alkyltrihalosilanes and tetrahalosilanes in the presence of an effective amount of a redistribution catalyst thereby forming a redistribution product comprising dialkyldihalosilane. At least a portion of the catalyst required for conducting the process may be formed in situ during direct process operation and isolation of the residue.

Alkylhalosilanes prepared by the direct process form a complex mixture which is typically distilled to separate methylchlorosilanes from other components present in the mixture. After the methylchlorosilanes are distilled from the mixture, remaining are monosilane, disilane and silalkylene by-product fractions. The disilane and silalkylene fractions which boil above about 80° C. are hereinafter referred to as "alkyl-rich silalkylene-containing residues." In current commercial operations for performing the direct process, the alkyl-rich silalkylene-containing residues alone can constitute as much as five weight percent of the resultant product. Therefore, it is desirable to treat the alkyl-rich silalkylene-containing residues to produce commercially desirable products to reduce by-product disposal and to improve raw material utilization.

The "direct process" is well described in the patent literature, for example, in Rochow, U.S. Pat. No. 2,380,995 and Barry et al., U.S. Pat. No. 2,488,487. The high-boiling fraction remaining after the monosilanes overhead distillation is a complex mixture comprising higher boiling silicon containing compounds which have, for example, SiSi, SiOSi, and SiCSi linkages in the molecules. The high-boiling fraction may also contain particulate silicon and metals or compounds thereof. Typical high-boiling fractions obtained from the direct process distillation product are described, for example, in Mohler et al., U.S. Pat. No. 2,598,435 and Barry et al., U.S. Pat. No. 2,681,355.

Wagner, U.S. Pat. No. 2,606,811, teaches a hydrogenation process where a compound containing a halogen and the Si-Si bond is heated to at least 300° C. in the presence of hydrogen. The resultant products are monosilanes.

Atwell et al., U.S. Pat. No. 3,639,105, describe a process where hydrosilanes are produced by contacting a disilane with hydrogen gas under pressure and heating the mixture in the presence of a transition metal catalyst such as palladium on charcoal. Atwell et al. state that the disilane may be part of a mixture from the direct process. Atwell et al. further report that when the disilane was a methylchlorodisilane, the resulting product contained about four to 28 weight percent methyltrichlorosilane. Generally, organotrihalosilanes such as methyltrichlorosilane have limited commercial usefulness and for this reason limit the usefulness of the process described by Atwell et al.

Neale, U.S. Pat. No. 4,079,071, describes a process for preparing hydrosilanes in high yields by reacting methylchloropolysilanes with hydrogen gas under pressure at a temperature from 25° C. to about 350° C. in the presence of a copper catalyst. Neale states that the methylchloropolysilanes can be those typically created as direct process by-products. Useful catalysts described by Neale include copper metal, copper salts, and complexes of copper salts with organic ligands. In some cases, Neale reports that up to 29 weight percent methyltrichlorosilane was formed.

Ritzer et al., U.S. Pat. No. 4,393,229, describe a process for converting alkyl-rich disilanes in residue obtained from the manufacture of alkylhalosilanes to halogen-rich polysilanes. The process comprises treating an alkyl-rich disilane-containing residue with an alkyltrihalosilane or silicon tetrahalide in the presence of a catalyst and a catalytic amount of a hydrosilane reaction promoter at an elevated temperature. Ritzer et al. teach aluminum trichloride as a useful catalyst in the process when used with a hydrosilane promoter. Ritzer et al. further teach that the resulting halogen-rich polysilanes can, in a separate step, be cleaved to form monosilanes.

Bokerman et al., U.S. Pat. No. 5,175,329, describe a process for the producing organosilanes from the high-boiling residue resulting from the direct process that results in a net consumption of organotrichlorosilane. In the process, the high-boiling residue is contacted with an organotrichlorosilane and hydrogen gas in the presence of a hydrogenation catalyst and a redistribution catalyst.

Ferguson et al., U.S. Pat. No. 5,430,168, describe a process for producing monosilanes from the high-boiling residue resulting from the "direct process." The process comprises forming a mixture comprising an organotrihalosilane and high-boiling residue in the presence of hydrogen gas and a catalytic amount of aluminum trichloride. The process results in organotrihalosilane consumption and conversion of the high-boiling residue to useful monosilanes.

The present invention provides a process for redistributing alkyl-rich silalkylene-containing residues resulting from the direct process for producing methylchlorosilanes. The present inventor has discovered that by contacting the alkyl-rich silalkylene containing residue with a halosilane selected from the group consisting of alkyltrihalosilanes and tetrahalosilanes in the presence of an effective amount of a redistribution catalyst that a redistribution product is produced containing halogen-rich silalkylenes and more valuable dialkyldihalosilanes. The present invention provides a process for improving the utilization of valuable alkyl groups from alkyl-rich silalkylene-containing residue obtained form the production of methylchlorosilanes while simultaneously converting the halosilanes to commercially more valuable dialkyldihalosilanes. At least a portion of the catalyst required for conducting the process may be formed in situ during the direct process operation and isolation of the residue.

SUMMARY OF INVENTION

The present invention is a process for redistributing an alkyl-rich silalkylene-containing residue. The process comprises contacting an alkyl-rich silalkylene-containing residue with a halosilane selected from the group consisting of alkyltrihalosilanes and tetrahalosilanes in the presence of an effective amount of a redistribution catalyst at a temperature within a range of about 150° C. to 500° C. thereby forming a redistribution product comprising dialkyldihalosilane.

DESCRIPTION OF INVENTION

The present invention is a process for redistributing an alkyl-rich silalkylene-containing residue. The process comprises contacting an alkyl-rich silalkylene-containing residue with a halosilane selected from the group consisting of alkyltrihalosilanes and tetrahalosilanes in the presence of an effective amount of a redistribution catalyst at a temperature within a range of about 150° C. to 500° C. thereby forming a redistribution product comprising dialkyldihalosilane.

The present process may be run in any standard pressurizable reactor suitable for contact with halosilanes. The process may be run as a batch process or as a continuous process. The process may be run, for example, in a continuous stirred-tank reactor, a bubble-column reactor, a trickle-bed reactor, or a plug-flow reactor.

In the present process as used herein, the alkyl-rich silalkylene-containing residue is the residue resulting from the reaction of methyl chloride with silicon metalloid and distillation of the methylchlorosilanes from the residue. By "alkyl-rich silalkylene" it is meant a silalkylene having alkyl groups but no halogen atoms or fewer halogen atoms than alkyl groups substituted on the silicon atoms of the molecule. Generally, a silalkylene is an alkyl-rich silalkylene when it has from 0 to 2 halogen atoms and preferably 3 to 6 alkyl groups. As used herein, a halogen-rich silalkylene is a silalkylene having halogen atoms but no alkyl groups or the same number or fewer alkyl groups than halogen atoms substituted on the silicon atoms of the molecule. Generally, the halogen-rich silalkylene has an equal number of halogen atoms and alkyl groups substituted upon the silalkylene molecule or has a greater number of halogen atoms than alkyl groups substituted upon the silicon atom of the silalkylene molecule. Generally, a halogen-rich silalkylene has 3 to 6 halogen atoms and preferably 0 to 2 alkyl groups substituted upon the silicon atoms of the silalkylene molecule.

The alkyl-rich silalkylene-containing residue comprises polymeric silicon containing compounds having a boiling point above 80° C. The polymeric silicon containing compounds may include disilanes, such as, $Me_2ClSiSiClMe_2$, $Me_2ClSiSiMeCl_2$, $MeCl_2SiSiMeCl_2$, and silmethylenes, such as $Me_2ClSiCH_2SiClMe_2$, $Me_2ClSiCH_2SiCl_2Me$, $Me_3SiCH_2SiMe_3$ and $MeCl_2SiCH_2SiCl_2Me$, and silethylenes, such as $Me_2ClSiCH_2CH_2SiMeCl_2$, $MeCl_2SiCH_2CH_2SiMeCl_2$, and $Me_2ClSiCH_2CH_2SiMeCl_2$. A typical composition for such an alkyl-rich silalkylene-containing residue comprises: 50-60 wt % of disilanes of formula $Si_2Q_6$, where each Q is independently selected from a group consisting of methyl and chlorine and the disilane contains two to four methyl substituents per molecule; 15 to 25 weight percent silmethylenes described by formula $Q_3SiCH_2SiQ_3$, where Q is as previously described and the silmethylene contains two to four methyl substituents per molecule; silalkylenes described by formula $Q_3Si(SiQ_2)_a(CH_2)_b(SiQ_2)_cSiQ_3$, where Q is as previously described, the silalkylene contains two to four methyl substituents per molecule, a=0 to 4, b=1 to 3, c=0 to 4, and a+b+c>1; 5 to 15 weight percent of other high-boiling silicon-containing compounds; catalysts carry over from the direct process such as copper and compounds of copper; particulate containing silicon; and low levels of metals such as aluminum, calcium, iron, and compounds thereof. For example, a typically weight percent composition of an alkyl-rich silalkylene-containing residue resulting from the reaction of methyl chloride with silicon metalloid is 4 wt % $Me_2ClSiSiClMe_2$, 31 wt % $Me_2ClSiSiMeCl_2$, 46 wt % $MeCl_2SiSiMeCl_2$, 1 wt % $Me_2ClSiCH_2SiClMe_2$, 3 wt % $Me_2ClSiCH_2SiCl_2Me$, 7 wt % $MeCl_2SiCH_2SiCl_2Me$, and 9 wt % catalyst carry over, particulate containing silicon and metals.

The alkyl-rich silalkylene-containing residues or the silalkylene portions are contacted with a halosilane selected from the group consisting of alkyltrihalosilanes and tetrahalosilanes or a mixture thereof. Generally, the alkyltrihalosilane reactant is compatible with the silalkylenes undergoing the redistribution reaction in the residue, and if the silalkylenes are chlorinated silalkylenes, then the alkyltrihalosilane reactant is preferably an alkyltrichlorosilane. The alkyltrihalosilanes include those having straight chain or branched alkyl groups comprising 1 to about 8 carbon atoms, and those wherein the halogen atoms are chlorine, bromine, fluorine, iodine, and mixtures thereof. Examples of alkyltrihalosilane include methyltribromosilane, methyltrifluorosilane, methyltrichlorosilane, ethyltribromosilane, ethyltrifluorosilane, ethyltrichlorosilane, ethyltriodosilane, n-propyltrichlorosilane, n-propyltribromosilane, n-propyltrifluorosilane, iso-propyltrichlorosilane, iso-propyltrifluorosilane, iso-propyltribromosilane, n-butyltrichlorosilane, and the like. The preferred alkyltrihalosilane is methyltrichlorosilane. The preferred tetrahalosilane is silicon tetrachloride. In an alternative embodiment, the alkyltrihalosilane is an alkyltrihalosilane produced as a direct process by-product and is present as a component of the residue and the alkyltrihalosilane can be used directly as a reactant in the process of the present invention.

The amount of alkyltrihalosilane or tetrahalosilane added to the present method may be the stoichiometric amount required to redistribute the alkyl-rich silalkylene-containing residue to halogen-rich silalkylenes, however, it is generally preferred to use a molar excess of the alkyltrihalosilane or tetrahalosilane or a mixture thereof to carry out the reaction with the silalkylenes in the residue. Preferably, the alkyltrihalosilane or tetrahalosilane, or a mixture thereof is added to the present process at about 0.5 mole to about 25.0 moles per mole of silalkylene present in the residue.

The catalysts useful in the present process are those catalysts which promote the redistribution of alkyl groups on silalkylene molecules with halogen atoms on monosilane molecules. Generally, Lewis Acids or equivalent may be used as a catalyst in the present process. Examples of catalysts that may be used in the process are zirconium tetrachloride, aluminum trichloride, potassium aluminum tetrachloride, cuprous chloride, boric acid, and boron trifluoride. The preferred catalyst for use in the present process is aluminum trichloride or compounds of aluminum trichloride.

The amount of catalyst useful in the present process is any amount effective in promoting redistribution of alkyl groups on silalkylene molecules with halogen atoms on monosilane molecules. The preferred catalyst concentration useful in the present process is in the range of about 0.05 to 15 weight percent of the combined weight of silalkylene in the residue and the alkyltrihalosilane or tetrahalosilane or a mixture thereof. Most preferred the catalyst concentration is in the range of about 0.5 to 15 weight percent on the same basis.

The catalyst may be added to the process as the compound or may be formed in situ by the addition of materials that contain such catalyst or their precursors. In the preferred process when the catalyst is aluminum trichloride or compounds of aluminum trichloride, all or a portion of the catalyst may be formed in situ during conducting the direct process. The aluminum trichloride catalyst amount can be a combination of added aluminum trichloride and in situ formed aluminum trichloride remaining in the mixture as isolated from the direct process.

The present process can be conducted at a temperature within a range of about 150° C. to 500° C. Preferred is a temperature within a range of about 250° C. to 400° C. Most preferred is a temperature within a range of about 320° C. to 380° C.

In an alternative embodiment of the invention, the alkyl-rich silalkylenes in the alkyl-rich silalkylene-containing residue may be separated from the disilanes by distillation. The redistribution may be conducted by contacting the alkyl-rich silalkylene with a halosilane selected from the group consisting of alkyltrihalosilanes and tetrahalosilanes in the presence of an effective amount of a redistribution catalyst at a temperature within a range of about 150° C. to 500° C. thereby forming a redistribution product comprising dialkyldihalosilane.

The preferred dialkyldihalosilane produced from the present process is dimethyldichlorosilane. The dimethyldichlorosilane can be separated from the halogen-rich silalkylenes by standard methods for separating liquid mixtures, for example, distillation.

The following examples are provided to illustrate the present invention. These examples are not intended to limit the claims herein.

EXAMPLE 1

The ability to redistribute an alkyl-rich silalkylene-containing residue with methyltrichlorosilane in the presence of in situ formed aluminum trichloride as catalyst was evaluated in a stirred-tank batch reactor. A mixture was formed comprising 77 grams of an alkyl-rich silalkylene-containing residue (ARSR) and 155 grams of methyltrichlorosilane. About 3 wt % of aluminum trichloride present in the mixture was formed in situ during preparation and isolation of monosilanes. The composition of the alkyl-rich silalkylene-containing residue is described in Table 1. The mixture (219 grams) was added to a 600 ml, stirred, Parr Bomb reactor and heated to about 350° C. for about one hour. The reactor contents were then vented to a cold receiver vessel. A 210 gram sample from the reactor was analyzed by gas chromatography using a thermal conductivity detector (GC-TCD). The ARSR composition, initial composition weight percent and analysis results indicated by the final composition weight percent are reported in Table 1.

TABLE 1

Alkyl-Rich Silalkylene-Containing Residue

| Composition | Initial Composition Weight % | Final Composition Weight % |
|---|---|---|
| MeHSiCl$_2$ | 0 | 1.5 |
| MeSiCl$_3$ | 70 | 52 |
| Me$_2$SiCl$_2$ | 1.6 | 12 |
| SiCl$_4$ | 0 | 0.5 |
| Me$_2$ClSiCH$_2$SiMeCl$_2$ | 4.3 | 0 |
| MeCl$_2$SiCH$_2$SiMeCl$_2$ | 5.7 | 10.5 |

EXAMPLE 2

The ability to redistribute an alkyl-rich silalkylene-containing residue with tetrachlorosilane in the presence of in situ formed aluminum trichloride as catalyst was evaluated in a stirred-tank batch reactor. A mixture was formed comprising 104 grams of an alkyl-rich silalkylene-containing residue (ARSR) and 127 grams of tetrachlorosilane. About a 4wt % of aluminum trichloride present in the mixture was formed in situ during preparation and isolation of monosilanes. The composition of the alkyl-rich silalkylene-containing residue is described in Table 2. The mixture (218 grams) was added to a 600 ml, stirred, Parr Bomb reactor and heated to about 350° C. for about one hour. The reactor contents were then vented to a cold receiver vessel. A 200 gram sample from the reactor was analyzed by GC-TCD. The ARSR composition, initial composition weight percent, and analysis results indicated by the final composition weight percent are reported in Table 2.

TABLE 2

Alkyl-Rich Silalkylene-Containing Residue

| Composition | Initial Composition Weight % | Final Composition Weight % |
|---|---|---|
| HSiCl$_3$ | 0 | 3.4 |
| MeSiCl$_3$ | 0 | 13 |
| Me$_2$SiCl$_2$ | 0 | 10 |
| SiCl$_4$ | 55 | 45 |
| Me$_3$SiCl | 0 | 0.2 |
| Me$_2$ClSiCH$_2$SiMeCl$_2$ | 4 | 0 |
| MeCl$_2$SiCH$_2$SiMeCl$_2$ | 5.5 | 8 |

EXAMPLE 3

The ability to redistribute a silethylene compound with methyltrichlorosilane in the presence of added aluminum trichloride as catalyst was evaluated in a stirred-tank batch reactor. A mixture was formed comprising 42 grams of 1,1,4,4-tetramethyl-1,4-dichlorodisilethylene purchased from United Chemical Technologies, Briston, Pa., USA and 109 grams of methyltrichlorosilane. The mixture (140 grams) and 7.5 grams of aluminum trichloride were added a 600 ml, stirred, Parr Bomb reactor and heated to about 350° C. for about one hour. The reactor contents were then vented to a cold receiver vessel. A 140 gram sample from the reactor was analyzed by GC-TCD. The silethylene composition, initial composition weight percent, and analysis results indicated by the final composition weight percent are reported in Table 3.

TABLE 3

Silethylene Compound

| Composition | Initial Composition Weight % | Final Composition Weight % |
|---|---|---|
| MeHSiCl$_2$ | 0 | 2.4 |
| Me$_3$SiCl | 0 | 0.8 |
| MeSiCl$_3$ | 72 | 33 |
| Me$_2$SiCl$_2$ | 0 | 31.5 |
| Me$_2$ClSiCH$_2$CH$_2$SiMeCl$_2$ | 0 | 4 |
| MeCl$_2$SiCH$_2$CH$_2$SiMeCl$_2$ | 0 | 4 |
| Me$_2$ClSiCH$_2$CH$_2$SiMe$_2$Cl | 28 | 0 |

EXAMPLE 4

The ability to redistribute a silmethylene compound with methyltrichlorosilane in the presence of added aluminum trichloride as catalyst was evaluated in a stirred-tank batch reactor. A mixture was formed comprising 51 grams of bis(trimethylsilyl)methylene purchased from Gelest, Incorporated, Tullytown, Pa., USA and 142 grams of methyltrichlorosilane. The mixture (180 grams) and 8 grams of aluminum trichloride were added to a 600 ml, stirred, Parr Bomb reactor and heated to about 350° C. for about one hour under hydrogen gas at 2900 kPa pressure. The reactor contents were then vented to a cold receiver vessel. A 183 gram sample from the reactor was analyzed by GC-TCD. The silethylene composition, initial composition weight percent and analysis results indicated by the final composition weight percent are reported in Table 4.

TABLE 4

Silmethylene Compound

| Composition | Initial Composition Weight % | Final Composition Weight % |
|---|---|---|
| $Me_2HSiCl$ | 0 | 0.4 |
| $MeHSiCl_2$ | 0 | 1.4 |
| $Me_3SiCl$ | 1 | 7 |
| $MeSiCl_3$ | 74 | 7 |
| $Me_2SiCl_2$ | 1 | 46.6 |
| $Me_3SiCH_2SiMe_3$ | 26 | 0 |
| $Me_2ClSiCH_2SiMe_2Cl$ | 0 | 1 |
| $MeCl_2SiCH_2SiMe_2Cl$ | 0 | 7 |
| $MeCl_2SiCH_2SiMeCl_2$ | 0 | 6.5 |

I claim:

1. A process for redistributing an alkyl-rich silalkylene-containing residue consisting essentially of contacting an alkyl-rich silalkylene-containing residue with a halosilane selected from the group consisting of alkyltrihalosilanes and tetrahalosilanes in the presence of an effective amount of a redistribution catalyst at a temperature within a range of about 150° C. to 500° C. thereby forming a redistribution product comprising dialkyldihalosilane.

2. A process according to claim 1 further comprising separating the dialkyldihalosilane from the redistribution product.

3. A process according to claim 1, where the alkyl-rich silalkylene-containing residue is a distillation fraction resulting from the distillation of the reaction product of methyl chloride with silicon metalloid.

4. A process according to claim 1, where the amount of the halosilane is the stoichiometric amount required to redistribute the alkyl-rich silalkylene-containing residue to halogen-rich silalkylenes.

5. A process according to claim 1, where there is a molar excess of the halosilane to the silalkylenes in the residue.

6. A process according to claim 1, where the amount of the halosilane is about 0.5 mole to 25.0 moles per mole of silalkylene in the residue.

7. A process according to claim 1, where the catalyst is a Lewis Acid.

8. A process according to claim 7, where the catalyst is selected from the group consisting of zirconium tetrachloride, aluminum trichloride, potassium aluminum tetrachloride, cuprous chloride, boric acid, and boron trifluoride.

9. A process according to claim 1, where the catalyst is aluminum trichloride.

10. A process according to claim 1, where the catalyst concentration is in the range of about 0.05 to 15 weight percent of the combined weight of silalkylene in the residue and the halosilane.

11. A process according to claim 1, where the catalyst concentration is in the range of about 0.5 to 15 weight percent of the combined weight of silalkylene in the residue and halosilane.

12. A process according to claim 8, where at least a portion of the catalyst is formed in situ.

13. A process according to claim 9, where at least a portion of the aluminum trichloride is formed in situ.

14. A process according to claim 1, where the temperature is within a range of about 250° C. to 400° C.

15. A process according to claim 1, where the temperature is within a range of about 320° C. to 380° C.

16. A process according to claim 1, where the tetrahalosilane is tetrachlorosilane.

17. A process according to claim 1, where the alkyltrihalosilane is methyltrichlorosilane.

18. A process for redistributing an alkyl-rich silalkylene consisting essentially of contacting an alkyl-rich silalkylene described by formulas $Q_3SiCH_2SiQ_3$, and $Q_3Si(SiQ_2)_a(CH_2)_b(SiQ_2)_cSiQ_3$, where each Q is independently selected from a group consisting of methyl and chlorine, the silalkylene contains two to four methyl substituents per molecule, a=0 to 4, b=1 to 3, c=0 to 4, and a+b+c>1;

with a halosilane selected from the group consisting of alkyltrihalosilanes and tetrahalosilanes in the presence of an effective amount of a redistribution catalyst at a temperature within a range of about 150° C. to 500° C. thereby forming a redistribution product comprising dialkyldihalosilane.

19. A process according to claim 18, where the catalyst is selected from the group consisting of zirconium tetrachloride, aluminum trichloride, potassium aluminum tetrachloride, cuprous chloride, boric acid and boron trifluoride.

20. A process according to claim 18, where the alkyl-rich silalkylene is selected from the group consisting of silylethylenes and silylmethylenes.

* * * * *